United States Patent [19]

Linder

[11] Patent Number: 4,789,543

[45] Date of Patent: Dec. 6, 1988

[54] NEUTRAL TECHNETIUM 99-M COMPLEXES USEFUL AS RADIODIAGNOSTIC AGENTS

[75] Inventor: Karen E. Linder, Somerville, Mass.

[73] Assignee: E. I. Du Pont de Nemours and Company, Wilmington, Del.

[21] Appl. No.: 676,932

[22] Filed: Nov. 30, 1984

[51] Int. Cl.[4] .................. A61K 49/02; C07F 13/00
[52] U.S. Cl. .......................... 424/1.1; 534/14
[58] Field of Search ............ 424/1.1, 9; 534/14; 422/61; 252/188.2, 188.21, 188.22, 188.23, 188.24, 645

[56] References Cited

U.S. PATENT DOCUMENTS

| | | | |
|---|---|---|---|
| 4,387,087 | 6/1983 | Deutsch et al. | 424/1.1 |
| 4,419,339 | 12/1983 | Neirinckx | 424/1.1 |
| 4,451,450 | 5/1984 | Subramanyam | 424/1.1 |
| 4,452,774 | 6/1984 | Jones et al. | 424/1.1 |
| 4,455,291 | 6/1984 | Tweedle | 424/1.1 |
| 4,489,054 | 12/1984 | Deutsch et al. | 424/1.1 |
| 4,497,790 | 2/1985 | Rodriguez | 424/1.1 |
| 4,512,967 | 4/1985 | Linder | 424/1.1 |
| 4,526,776 | 7/1985 | Subramanyam et al. | 424/1.1 |
| 4,615,876 | 10/1986 | Troutner et al. | 424/1.1 |

*Primary Examiner*—John F. Terapane
*Assistant Examiner*—J. E. Thomas

[57] ABSTRACT

An hepatobiliary imaging agent is disclosed which is a neutral complex of Tc-99m, a complexing ion, $SO_2$, and a mono or polydentate organic ligand having one or more donor atoms for complexing with TC-99m to form the neutral complex.

2 Claims, No Drawings

NEUTRAL TECHNETIUM 99-M COMPLEXES USEFUL AS RADIODIAGNOSTIC AGENTS

FIELD OF THE INVENTION

The present invention relates to neutral $^{99m}$Tc-labelled radiodiagnostic agents, kits for preparing such $^{99m}$Tc-labelled radiodiagnostic agents, and methods for using such $^{99m}$Tc-labelled radiodiagnostic agents.

BACKGROUND OF THE INVENTION

Various complexes of monodentate and bidentate ligands with technetium having been made and studied. These complexes generally were made for use in studies to determine the various oxidation states of technetium and for other research regarding the structure of such complexes and metal-coordination chemistry. Such studies have been reported in, for instance, *Chemistry and Industry*, pp. 347–8 (Mar. 26, 1960); *J. Inorg. Nucl. Chem.*, Vol. 28, pp. 2293–96 (1966); *Aust. J. Chem.*, 23, pp. 453–61 (1970); *Inorganic Chem.*, Vol. 16, No. 5, pp. 1041–48 (1977); *J. Inorg. Nucl. Chem.*, Vol. 39, pp. 1090–92 (1977); and *J. C. S. Dalton*, pp. 125–30 (1976).

In a presentation to the American Pharmaceutical Association, E. A. Deutsch disclosed that certain complexes of DIARS, i.e.

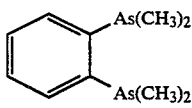

and Tc-99m, and certain complexes of DMPE, i.e. $(CH_3)_2PCH_2CH_2P(CH_3)_2$ and Tc-99m, may be useful as radio-diagnostic agents for myocardial and hepatobiliary imaging. $(^{99m}Tc\text{-}(DMPE)_2Cl_2)+$ and $[^{99m}Tc\text{-}(DIARS)_2Br_2]+$ were prepared by Deutsch by heating in an open flask a reaction mixture containing the appropriate hydrogen halide in aqueous alcohol solution, $^{99m}$Tc-sodium pertechnetate, and ortho-phenylenebis(-dimethylarsine), i.e. DIARS, orbis-(1,2-dimethylphosphino)ethane, i.e. DMPE. The reaction was reported to take about 30 minutes. The labelled complex was then purified by chromatographic methods involving ion exchange columns.

The labelled complex produced according to the procedure of Deutsch has several practical disadvantages. The procedure requires handling several ingredients including an organic solvent to make the reaction mixture and then purifying the resulting radiolabelled complex by chromatography. Each of these handling steps can contaminate the system and final product. The purification step further requires additional time for preparation of the final product. These steps require a skilled technician and are performed at the site of use, just prior to use. Thus, a complex, time consuming chemical preparation is required during which sterility of ingredients and containers is difficult to maintain. Thus, to assure freedom from contamination, a final sterilization step is required, which further adds to preparation time. Because Tc-99m has a short half-life, lengthy preparation methods are undesirable. Thus, the complexity of the preparation, both with regard to maintaining sterile conditions and to purification of the $^{99m}$Tc-labelled complex make the Deutsch procedure undesirable.

Certain commercially available hepatobiliary imaging agents, such as $^{99m}$Tc-labelled disofenin, take up to thirty (30) minutes to obtain an image of the hepatobiliary transit. It is desirable to have hepatobility agents with faster blood clearance rates that would enable the visualization of the hepatobiliary transit in less time.

SUMMARY OF THE INVENTION

The present invention provides a new hepatobiliary transit imaging agent that provides usable visible images in as little as ten minutes. The new hepatobiliary imaging agent is a neutral complex of (i) Tc-99m, (ii) a member of the group consisting of Cl, Br, I and SCN, hereinafter referred to as the "complexing ion", (iii) (SO$_2$), and (iv) a mono or polydentate organic ligand having one or more donor atoms for complexing with Tc-99m to form a neutral complex.

The present invention also provides a kit for making a hepatobiliary imaging agent wherein the kit preferably contains (i) a water soluble salt of the complexing ion, (ii) a compound that is capable of liberation of SO$_2$ gas upon decomposition such as Na$_2$S$_2$O$_4$, NaHSO$_3$, Zn-dithionite, formamide sulfinic acid (FSA), or coordination complexes containing labile SO$_2$, and (iii) a mono or polydentate organic ligand having one or more donor atoms for complexing with Tc-99m to form a neutral complex. Preferably, these compositions are contained in one or more sterile containers or vials.

The hepatobiliary imaging agent kit is used by adding 99mTc-sodium pertechnetate to the compositions above to form a neutral complex. Typically, the complex is formed at elevated temperatures (above room temperature).

The hepatobiliary imaging agent of this invention is used by injecting the neutral complex intravenously into a mammal, and positioning the mammal under a scintillation camera to obtain images of the hepatobiliary transit.

DETAILED DESCRIPTION OF THE INVENTION

The neutral technetium complexes of the present invention are preferably made by admixing the organic ligand, the complexing ion, the SO$_2$ liberating composition, and $^{99m}$Tc-sodium pertechnetate in a liquid carrier at a pH greater than about 1.5, and heating the admixture above room temperature for a period of time to cause the formation of a neutral complex of the ligand, complexing ion, SO$_2$, and Tc-99m.

Organic ligands useful in the practice of the present invention include those having the following structural formulas:

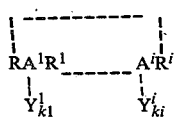

wherein:
i is an integer from 1 to 6;
R, R$^1$, R$^2$, R$^3$, R$^4$, R$^5$ and R$^6$ are each independently selected from hydrogen or substituted or unsubstituted alkyl, aryl, alkylaryl, arylalkyl, monocycloalkyl, polycycloalkyl, heterocyclic, carbocyclic, alkoxy, aryloxy and alkyl-amino groups, and R plus R$^i$ may be taken together to form a cyclic compound or separately to form a linear compound;

$Y^1$, $Y^2$, $Y^3$, $Y^4$, $Y^5$ and $Y^6$ are independently selected from substituted or unsubstituted alkyl, aryl, alkylaryl, arylalkyl, monocycloalkyl, polycycloalkyl, heterocyclic, carbocyclic, alkoxy, aryloxy and alkyl-amino groups;

$A^1$, $A^2$, $A^3$, $A^4$, $A^5$ and $A^6$ are the same or different donor atoms, each having a free-electron pair available for accepting a proton to provide a charged ligand or for complexing with Tc-99m or Tc-99 to form a neutral complex; and $k_1$, $k_2$, $k_3$, $k_4$, $k_5$ and $k_6$ are each independently zero or one;

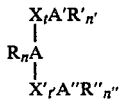  III wherein:

R, R' and R" are independently selected from hydrogen or substituted or unsubstituted alkyl, aryl, alkylaryl, arylalkyl, monocylcloalkyl, polycycloalkyl, heterocyclic and carbocyclic groups;

A, A' and A" are independently selected from the group of donor atoms having a pair of electrons available for accepting a proton to provide a charged ligand or for complexing with Tc-99m or Tc-99 to form a neutral complex; and X and X' are saturated or unsaturated alkyl groups;
n, n' and n" are independently the integer 1 or 2;
t and t' are independently 0 or 1; or

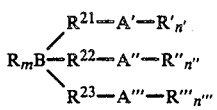  IV wherein:

R', R", and R''' are each independently selected from hydrogen or substituted or unsubstituted alkyl, aryl, alkylaryl, arylalkl, monocycloalkyl, polycycloalkyl, heterocyclic, carbocyclic, alkoxy, aryloxy and alkyl-amino groups;

A', A" and A''' are independently selected from the group of donor atoms having a pair of electrons available for accepting a proton to provide a charged ligand complexing with Tc-99m or Tc-99 to form a neutral complex;

B is an atom selected from the group of donor atoms having a pair of electrons for complexing with Tc-99m or Tc-99, boron or from the elements listed in Group IV A of the periodic table (i.e. C, Si, Ge, Sn, and Pb);

m is 0 or 1;
n', n", and n''' are independently the integer 1 or 2.

The R's and X's in formulas (II), (III) and (IV) are preferably alkyl radicals having 1 to about 6 carbon atoms such as methyl, ethyl, etc., and the like, and aryl radicals such as benzyl, phenyl, etc., and the like. When more than one R group is attached to the same donor atom, the R groups so attached can be the same or different. Typical examples of such ligands include, for instance, aryl compounds having arsenic, phosphorus, nitrogen, sulfur, oxygen, selenium, tellurium, or any combination of them, substituted ortho to each other. For example, o-phenylene compounds having the structure:

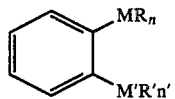  V in which M and M' are arsenic, phosphorus, nitrogen, sulfur, oxygen, selenium, tellurium, or any combination of them, n and n' are independently 1 or 2 depending upon the particular donor atom used for M and M', and R and R' are independently hydrogen, or an organic group, preferably in alkyl group having 1 to 6 carbon atoms, an aryl group such as phenyl, or the like, and substituted such groups. Additional examples of suitable ligands include bidentate cis-tetraethylene ligands of the formula:

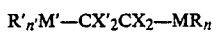  VI in which M, M', R, and R' are as defined above, n and n' are independently 1 or 2 depending upon the particular donor atom used for M and M', and X and X' are independently selected from hydrogen, halide, or substituted or unsubstituted lower alkyl groups having 1 to about 6 carbon atoms. Further examples of suitable ligands include those having the formula:

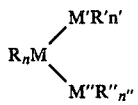  VII where M, M', R, and R', are as defined above, M" is independently selected from arsenic, phosphorous, nitrogen, sulfur, oxygen, selenium, and tellurium, and n is 0 or 1, n' and n" are independently 0, 1 or 2, and R" is independently selected from hydrogen, halide or an organic radical, preferably an alkyl radical having 1 to about 6 carbon atoms, an aryl radical such as phenyl, or the like, and substituted such groups.

Particularly preferred ligands for the practice of this invention are the bis-dialkylphosphinoethanes and their substituted derivatives, including, for example,
1,2-bis(dimethylphosphino)ethane,
1,2-bis(di(trifluoromethyl)phosphino)ethane,
1,2-bis(dimethylphosphino)-1,1-difluoroethane,
1,2-bis(dimethylphosphino)-1-fluoroethane,
1,2-bis(dimethylphosphino)propane,
1,2-bis(di(trifluoromethyl)phosphino)-1,1,2,2tetrafluoroethane,
1,2-bis(di(trifluoromethyl)phosphino)propane,
2,3-bis(di(trifluoromethyl)phosphine)butane,
1,2-bis(di(trifluoromethyl)phosphino)butane,
1,3-bis(dimethylphosphino)butane,
1,3-bis(dimethylphosphino)propane,
1,3-bis(di(trifluoromethyl)phosphino)propane,
1,2-bis(dimethylphosphino)-1,1-dichloro-2,2-difluoroethane,
1,2-bis(dimethoxyphosphino)ethane
1,2-bis(di(dimethylamino)phosphino)ethane
trimethylphosphite and similar compounds wherein the phosphorus is replaced by nitrogen, arsenic, sulfur, oxygen, selenium, tellurium, or another atom having a free electron pair, and the like.

Other useful ligands include the alkylaminobis(difluorophosphine), i.e., $RN(PF_2)_2$, ligands and the like where R is an organic group, preferably an alkyl group having 1 to about 6 carbon atoms, an aryl group as phenyl, or the like, and substituted such groups; the o-phenylene compounds such as, for example, orthophenylenebis(diarsine), orthophenylenebis(dimethylarsine), orthophenylenebis(diamine), orthophenylenebis(dimethylamine, orthophenylenebis(diphosphine), orthophenylene-bis(dimethylphosphine), and the like; and the isonitrile complexes described in U.S. Pat. No. 4,446,123 hereby incorporated by reference.

Additional ligands suitable for use in the present invention are those described by Nuzzo et al., in J. Amer. Chem. Soc., 101, p. 3683 (1979) and by Wilson et al., J. Amer. Chem. Soc., 100, p. 2269 (1978), which are hereby incorporated by reference.

Any donor element can be used in the ligand in accord with this invention provided that it has the capability of complexing with technetium (Tc-99 or Tc-99m) to form a neutral complex in the presence of suitable anions. Suitable such elements include, for instance, Carbon (C), phosphorous (P), arsenic (As), nitrogen (N), oxygen (O), sulfur (S), antimony (Sb), selenium (Se), tellurium (Te), and the like. Preferred elements are C, P and As.

The organic ligands described above are preferably used in the form of a water-soluble ligand, most preferably an acid salt, such as described in copending application Ser. No. 311,770 filed on Oct. 15, 1981, now U.S. Pat. No. 4,451,450 in the name of Vinayakam Subramanyam, which is incorporated herein by reference.

The neutral technetium complexes useful for radiodiagnostic treatments can be prepared by mixing in an aqueous or alcoholic solution the organic ligand or its acid salt and $^{99m}$Tc-pertechnetate in the presence of a complexing ion and $SO_2$ and heating the mixture to form the neutral complex.

Preferably the complexing ion is Cl provided as normal saline and the $SO_2$ is provided as compounds capable of releasing $SO_2$ gas, perferably Zn dithionite, FSA, $NaHSO_3$, sodium meta-bisulphate or coordination complexes containing labile $SO_2$. These ingredients are preferably provided as lyophilized compositions in a kit, such as a pre-sterilized vial. The pre-sterilized vial, such as a glass vial, containing these ingredients is ready for use for preparing neutral technetium complexes for radiodiagnostic use. Of course, the ingredients can be in separate vials, if so desired. In such lyophilized kits, the organic ligand is generally present as a water-soluble acid salt of the ligand.

The pertechnetate solution can then be injected into the vial under aseptic conditions to maintain sterility. The vial is generally heated and maintained at an elevated temperature for sufficient time to form a complex of the ligand, the complexing ion, and $SO_2$ with technetium. The vial should be at room temperature, preferably heated to at least 60° C. or more.

The organic ligand, salt of the complexing ion and $SO_2$ liberating compound for making neutral hepatobiliary complexes of the present invention are preferably supplied in a radiopharmaceutical preparation kit comprising a sterilized unit (or multiple) dose via containing the purified reactants. About 50 mCi of $^{99m}$Tc-pertechetate in saline is injected aspetically into the unit dose vial and the mixture heated to form the labelled neutral complex. After cooling, the resulting radiopharmaceutical preparation may be adjusted for pH and is ready for use. Typically, when the pH is adjusted, it is adjusted into the range of from 4.0 to about 9.0, and preferably to physiological pH.

To image the hepatobiliary transit of a mammal, a radiopharmaceutical preparation in accord with the invention, having a suitable quantity of radioactivity for the particular mammal, is injected intravenously into the mammal. The mammal is positioned under a scintillation camera in such a way that the hepatobiliary system is covered by the field of view. High quality images are obtained analogous to those seen in clinical studies using Disofenin.

This invention will be further illustrated by the examples that follow:

Preparation of 1,2-Bis(dimethylphosphino)ethane bis-bisulfate, i.e. [$DMPEH_2$]$^{2+}$.$2HSO_4^-$ or $DMPE.2H_2SO_4$ Dissolve 470 mg of DMPE in 10 ml of ethanol in a 50 ml round-bottomed flask maintained under a nitrogen atmosphere. From a glass syringe, add, with stirring, 0.34 ml of concentrated sulfuric acid. After 10 minutes, filter the precipitate and recrystallize it from 10 ml. of methanol. Filter and dry under vacuum. 920 mg of a crystalline solid is obtained, which melts at 135–136.5 C. Structure and purity of the compound DMPE bis(bisulfate) was confirmed by its infra-red and nuclear magnetic resonance spectra and elemental analysis.

Preparation of—$DMPE.2H_2SO_4$ Kit Product

Dissolve 5 g mannitol and 230 mg DMPE-bis(bisulfate) as prepared above in about 35 ml low-oxygen distilled water, and adjust the pH of the solution to 1.0 with 3N sulfuric acid. Under cover of nitrogen, and with stirring, add low-oxygen distilled water gravimetrically, to a solution weight of 50 g. Dispense 1 ml of this solution into each of several 10 cc vials. Freeze-dry in keeping with procedures well-known to those skilled in the art, stoppering under nitrogen.

EXAMPLE 1

Preparation of $^{99m}$Tc(DMPE)$_2$(SO$_2$)Cl—DMPE Complexes

Dissolve 50 mg of $DMPE.2H_2SO_4$ and 50 mg formamidine sulfinic acid (FSA) in 50 ml of low oxygen distilled water. Adjust to pH 1.8±0.2 via HCL. Dispense 1.6 ml of this solution into a 10 cc. vial under cover of nitrogen. Add 0.4 ml of $^{99m}$TcO$_4^-$ in normal saline and crimp seal the vial. Heat at 100° C. for 15 minutes in a boiling water bath. After cooling, analysis shows a labelled complex which has an HPLC retention time which is identical to that of authentic $^{99}$Tc(DMPE)$_2$(SO$_2$)Cl and which has neutral characteristics by electrophoresis.

EXAMPLE 2

Alternative Preparation of $^{99m}$Tc(DMPE)$_2$(SO$_2$)Cl—DMPE Complex

To the freeze-dried (but not as yet labelled) preparation of $DMPE.2H_2SO_4$ as described above is added 1 ml of physiological saline containing 10–20 mCi $^{99m}$Tc-pertechnetate and 5 microliters of $SO_2$-saturated saline. The formulation is boiled for 30 minutes at 100° C. HPLC analysis reveals a labelled complex identical to the complex of Example 1.

EXAMPLE 3

Visualization of Hepatobiliary Transit with $^{99m}$Tc-labelled Disofenin (Prior Art)

A lyophylized vial of HEPATOLITE TM (New England Nuclear Corporation's brand of Technetium Tc$^{99m}$ Disofenin) is labelled with $^{99m}$Tc-pertechnetate in accordance with manufacturer's directions. At least 1 mCi of the labelled preparation is injected intravenously into a 2.5 Kg male New Zealand Albino rabbit. The rabbit is positioned under a Searle Pho-Gamma scintillation camera in such a way that the liver and gastro-intestinal tract are within the field of view. Sequential images taken from the time of injection demonstrate an initial liver uptake with gradual visualization of the gall bladder and gastro-intestinal tract, analogous to the diagnostically efficacious results obtained in clinical studies of normal healthy humans.

EXAMPLE 4

Visualization of Hepatobiliary Transit with $^{99m}$Tc-Cl(SO2) Complexes

Greater than 1 mCi of the $^{99m}$Tc-Cl(SO$_2$)-DMPE complex from either Example 1 or 2 is injected into a rabbit as in Example 3. Sequential images of hepatobiliary transit reveal rapid passage and comparable image quality of the liver, gall bladder and gastro-intestinal tract in about 10 minutes as compared to about 30 minutes for Disofenin.

This invention has been described in detail with particular reference to the preferred embodiments thereof. However, it will be appreciated that those skilled in the art, upon reading this disclosure, may make modifications and improvements within the spirit and scope of the invention.

I claim:

1. A neutral radiodiagnostic agent comprising a complex of (1) Tc-99m, (ii) a complexing ion selected from Cl, Br, I and SCN, (iii) SO$_2$ and (iv) a mono- or polydentate organic ligand having a formula selected from:

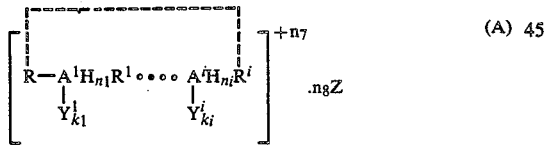

(A)

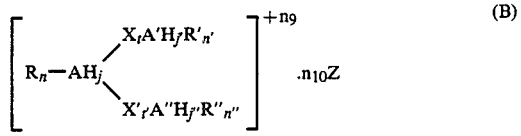

(B)

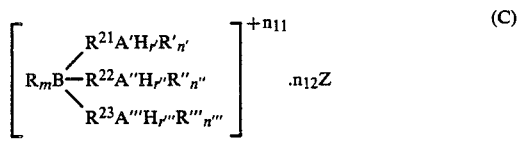

(C)

wherein:

R, R', R'', R''', R$^1$, R$^2$, R$^3$, R$^4$, R$^5$, R$^6$, R$^{21}$, R$^{22}$ and R$^{23}$ are each independently selected from hydrogen; or substituted or unsubstituted alkyl, alkylene, aryl, alkylaryl, arylalkyl, monocycloalkyl, polycycloalkyl, heterocyclic and carbocyclic group, and R plus R' in formula (A) may be taken together to form a cyclic compound;

A, A', A'', A$^1$, A$^2$, A$^3$, A$^4$, A$^5$ and A$^6$ are independently selected donor atoms, each having a free electron pair available for accepting a proton to provide a charged ligand and having the capability of complexing with Tc-99m to form a neutral complex;

B is an atom selected from the group of donor atoms having a pair of electrons for complexing with Tc-99m or Tc-99, boron or from the elements listed in Group IVA of the periodic table;

Y$^1$, Y$^2$, Y$^3$, Y$^4$, Y$^5$ and Y$^6$ are independently selected from hydrogen; or substituted or unsubstituted alkyl, alkylene, aryl, alkylaryl, arylalkyl, monocycloalkyl, polycycloalkyl, heterocyclic and carbocyclic groups; X and X' are saturated or unsaturated alkyl groups; Z is an anion; i is an integer from 1 to 6, j, j' and j$_i$ are each independently 0 or 1; k$^1$, k$^2$, k$^3$, k$^4$, k$^5$ and k$^6$ are each independently 0 or 1; n, n' and n'' are each independently the integer 1 or 2; n$_1$, n$_2$, n$_3$, n$_4$, n$_5$, n$_6$ are independently 0 or 1; n$_7$ and n$_8$ are each an integer from 1 to 6; n$_9$, n$_{10}$ and n$_{12}$ are each an integer from 1 to 3; m is 0 or 1; r', r'' and r''' are independently 0 or 1; and t and t' are independently 0 or 1.

2. The agent of claim 1 wherein the complexing agent is Cl.

* * * * *